US00PP22829P3

(12) United States Plant Patent
VanLaeken

(10) Patent No.: US PP22,829 P3
(45) Date of Patent: Jul. 3, 2012

(54) ***CLEMATIS* PLANT NAMED 'ANDREW VANLAEKEN'**

(50) Latin Name: ***Clematis* sp.**
Varietal Denomination: Andrew VanLaeken

(76) Inventor: James P VanLaeken, Walworth, NY (US)

( * ) Notice: Subject to any disclaimer, the term of this patent is extended or adjusted under 35 U.S.C. 154(b) by 0 days.

(21) Appl. No.: 12/807,755

(22) Filed: Sep. 14, 2010

(65) Prior Publication Data

US 2012/0066806 P1 Mar. 15, 2012

(51) Int. Cl.
*A01H 5/00* (2006.01)

(52) U.S. Cl. ..... Plt./228

(58) Field of Classification Search ..... Plt./228
See application file for complete search history.

*Primary Examiner* — Susan McCormick Ewoldt

(57) ABSTRACT

A new variety of *clematis* plant named 'Andrew VanLaeken'. The variety is characterized by it's very large flowers with nice color combinations of light purple with reddish veins and healthy dark green foliage. Andrew VanLaeken has a long blooming period and is a strong grower making it easy to propagate.

1 Drawing Sheet

Botanical classification: *Clematis* sp.
Cultivar designation: 'Andrew VanLaeken'.

BACKGROUND OF THE VARIETY

The present invention relates to a new and distinct variety of hybrid *clematis* plant known by the cultivar name 'Andrew VanLaeken'.

The new variety was a chance seedling found in a controlled planting of seedlings in a greenhouse in Walworth, N.Y. in 2003. Seeds were planted and this variety was picked out because of it's unique color combination, huge flower size and lush dark green foliage. This variety was asexually propagated by soft wood cuttings and observed over the next five years. Asexual propagation by vegetative cuttings has shown that the propagules are identical to the original plant and all distinguished characteristics. The stability of the variety is evidenced by the distinguished characteristics remaining true to form from generation to generation.

SUMMARY OF THE INVENTION

Among the features which distinguish the new variety from other present available and known commerical *clematis* cultivars are the unique color variations. The flower is bluish purple with reddish veins. The stamens are white filaments and reddish anthers. The lush dark green foliage and large blooms make this a desirable plant.

RELEVANT PRIOR ART

This new variety is similar to *Clematis* sp. 'Prince Phillip' that is a non patented variety. *Clematis* sp. 'Andrew VanLaeken' has more overlapping tepals also the foliage is a much darker green and has more flowers per plant.

BRIEF DESCRIPTION OF THE PHOTOGRAPH

The accompanying photograph illustrates the overall appearance of the new variety. The flowering and foliage colors as shown are, within the limitations of color photography, accurate and true reproductions of the actual colors of new variety.

The photographic view is a front elevation of typical *Clematis* sp. 'Andrew VanLaeken'.

BOTANICAL DESCRIPTION

The following information is based on a three year old plant grown in 50% shade in a five gallon container in a covered greenhouse with 60° F. ambient night temperatures and 75° F. ambient day temperatures in Walworth, N.Y. Color references are based on using the PANTONE® matching system.

1. Plant:
   - *A. Form.*—Upright climbing or spreading, no lateral branching was observed.
   - *B. Growth.*—Vigorous, vining. 1. Height: approximately 8 feet to 10 feet. 2. Diameter/Spread: approximately 2 feet to 3 feet.
   - *C. Foliage.* —Deciduous, compound-trifoliate, opposite. 1. Size, typical and observed: a. compound leaf length 4.5 inches, width 5 inches. b. individual leaflets length 2.5 to 3 inches, width 0.75 to 1.5 inches. c. leaflets per compound leaf: 3. 2. Quantity of leaves per stem: typically and observed: about 48. 3. Color. a. upper surface: dark green (PANTONE® #574U). b. lower surface: medium green (PANTONE® #575U). 4. Shape. a. leaflets: the overall appearance of the leaf on plant is more lancelot compared to other *clematis,* margin is untoothed with pubescent edge, apex is pointed. 5. Texture. a. upperside: smooth and veined. b. underside: ribbed and pubescent on veins and edges. c. venation pattern: leaflets palmatic with green coloration on upper and lower. 6. Petiole. a. color: light green (PANTONE® #583U). b. length, typical and observed: 1 to 2 inches. c. diameter, typical and observed: 1/16 inch. d. glabrous: no.
   - *D. Wood.*—1. New Shoots a. color: light green (PANTONE® #583C) with a reddish black tint (PANTONE® #696C). b. bark: pubescent. c. internodes: cylindrical, approximately 3 to 5 inches in length and 1/16 inch in diameter. 2. Old Wood. a. color: medium to dark brown (PANTONE® #4705C). b. bark: smooth 1/8 inch in diameter. c. internodes: cylindrical, approximately 5 to 6 inches in length and 1/8 inch in diameter and pubescent.

*E. Hardiness*. —US Zones 4 through 8. 1. low temperature tolerance, typical and observed: −10° F. to 0° F. 2. high temperature tolerance, typical and observed: 90° F. to 110° F.; requires 6 to 8 weeks dormancy at 35° F. to 40° F. to remain vigorous.

*F. Disease*.—1. Subject to any disease that affects *clematis*. a. wilt. b. botrytis. c. powdery mildew.

*G. Pests*.—1. Subject to any pest that normally affect *clematis*. a. aphids. b. spider mites. c. slugs and snails.

II. Flower:

*A. Blooming habit*.—May and June on new growth based on climate in Rochester, N.Y. area.

*B. Bud*.—1. Size: typical and observed from about 1.75 to 2.25 inches in length and about 1/2 to 1 inch in diameter. 2. Form: ovate base with pointed tip. 3. Color: light green (PANTONE® #577C) with purplish veins (PANTONE® #5205C).

*C. Stem*.—1. Dimension, typical and observed: length 1.5 inches, diameter 1/16 inch. 2. Aspect: vertical. 3. strength: erect. 4. Color: light green (PANTONE® #577C) with purple shading (PANTONE® #5205C).

*D. Bloom*.—1. Size: typical and observed from about 6 to 8 inches in diameter with a depth of about 3/4 inch. 2. Form: round shaped with 6 to 9 tepals of equal size slightly overlapping. 3. Color upper surface: bluish purple (PANTONE® #257U) with reddish bar (PANTONE® #237U). 4. Color of lower surface: outer edge is light purple (PANTONE®#2715U) middle is white with prominent veins. 5. Characteristics: born on 1.5 to 2 inch stems on new and old growth. 6. Quantity: 1 bloom per stem from 2 or 3 to several hundred blooms per plant depending on the age and size of plant. 7. lastingness: 3 to 6 days as a cut flower or 7 to 10 days on plant.

*E. Tepals*.—1. Form: elliptical shape, narrow at base rounding at mid section width 1.5 inches to 1.75 inches at widest point and then tapering down to a pointed apex. The overall tepal length being 3 to 4 inches. 2. Arrangement of tepals: regularly arranged slightly overlapping. 3. Fragrance: none. 4. Color: upper surface bluish purple (PANTONE® #257U) with reddish bar (PANTONE® #237U) lower surface on outer edge is light purple (PANTONE®#2715U) middle is white with prominent veins.

III. Reproductive Organs:

*A. Stamens, filaments and anthers*.—1. Arrangement: irregularly arranged. 2. Stamens: typical and observed 40 to 50 per bloom, length 0.75 inch. 3. Anthers: length 1/4 to 3/8 inch (PANTONE® #198U) reddish. 4. Filament: white.

*B. Pollen*.—1. Color: white. 2. Amount: scarce.

*C. Styles*.—White, even, average length.

*D. Stigmas*.—1. Color: white.

*E. Seed, typical and observed*.—1. Diameter: 1/16 inch. 2. Thickness: 1.32 inch. 3. Color: (PANTONE® #576U) medium green. 4. Shape: round. 5. Quantity per bloom: 20 to 30. 6. Description: 3/4 inch long persistent style which is clothed with silky white hairs.

I claim:

1. A new and distinct variety of *clematis* plant named 'Andrew VanLaeken' as shown and described herein.

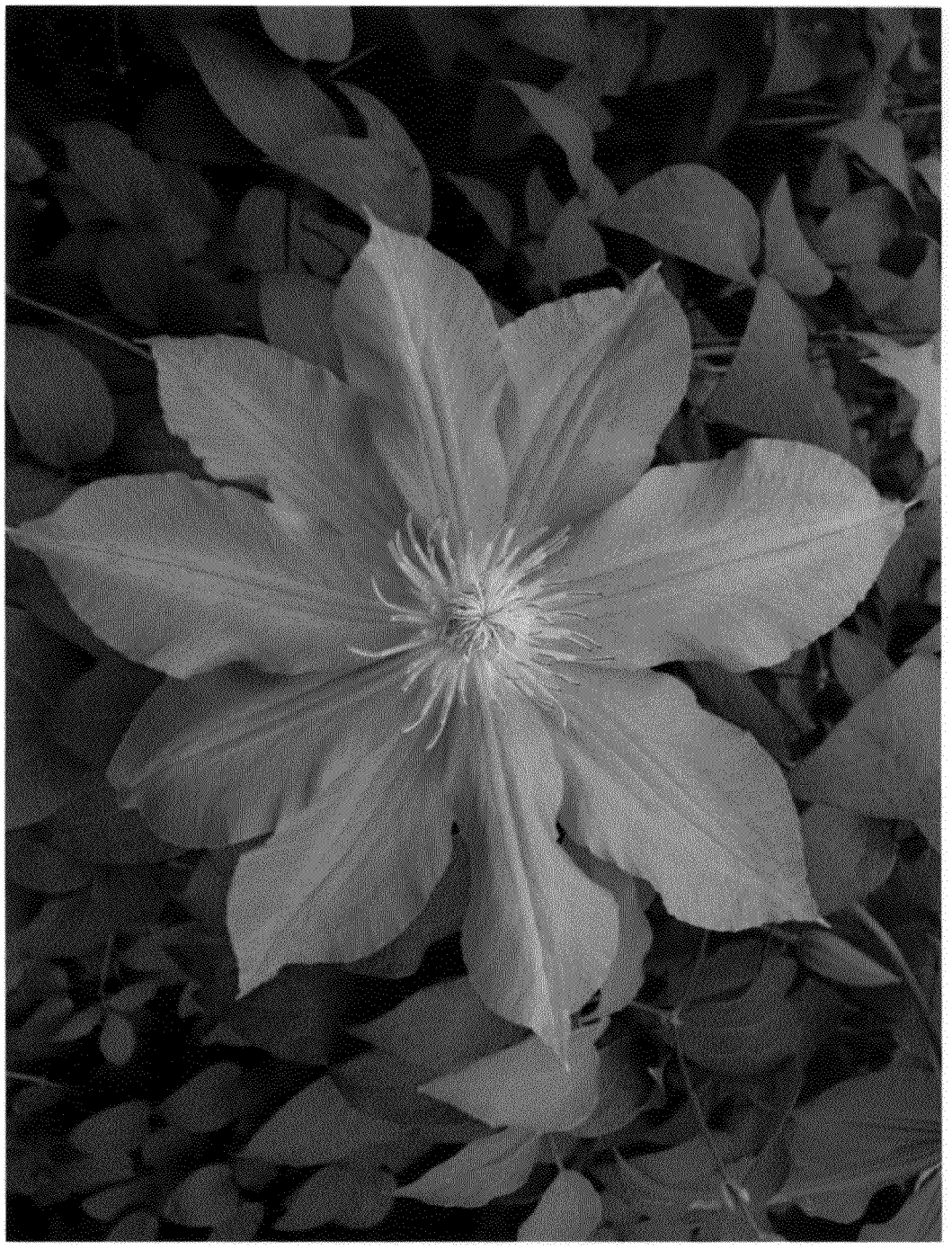

* * * * *